United States Patent
Bax et al.

(10) Patent No.: US 10,837,597 B2
(45) Date of Patent: Nov. 17, 2020

(54) COUNTERBALANCING APPARATUS FOR GIMBAL JOINTS AND/OR A METHOD FOR COUNTERBALANCING A LOAD ON A GIMBAL JOINT

(71) Applicant: Aaron Fenster, London (CA)

(72) Inventors: Jeffrey Bax, London (CA); Kevin Barker, London (CA); Dandan Shan, London (CA); Christopher Waring, London (CA); Aaron Fenster, London (CA)

(73) Assignee: Aaron Fenster, London (CA)

( * ) Notice: Subject to any disclaimer, the term of this patent is extended or adjusted under 35 U.S.C. 154(b) by 0 days.

(21) Appl. No.: 15/563,019

(22) PCT Filed: Mar. 31, 2015

(86) PCT No.: PCT/CA2015/000204
§ 371 (c)(1),
(2) Date: Sep. 29, 2017

(87) PCT Pub. No.: WO2016/154709
PCT Pub. Date: Oct. 6, 2016

(65) Prior Publication Data
US 2018/0051850 A1    Feb. 22, 2018

(51) Int. Cl.
*A61B 8/00*   (2006.01)
*F16M 11/12*  (2006.01)
(Continued)

(52) U.S. Cl.
CPC ............... *F16M 13/02* (2013.01); *A61B 8/44* (2013.01); *F16M 11/08* (2013.01);
(Continued)

(58) Field of Classification Search
USPC ............ 248/323, 324, 325, 327, 330.1, 331, 248/123.11, 123.2, 162.1, 406.2
See application file for complete search history.

(56) References Cited

U.S. PATENT DOCUMENTS 2,832,159 A * 4/1958 Frick ...................... D06F 77/00
                                                       38/30
3,369,408 A * 2/1968 Bach .................... G01B 5/0002
                                                       73/866.5
(Continued)

FOREIGN PATENT DOCUMENTS

GB         320355 A      10/1929

OTHER PUBLICATIONS

Sharon Joines, Tamara James, and Gisela Suarez. "Upper Extremity Pain in." Advances in Human Factors and Ergonomics in Healthcare (2010): 114. (10 pages total).
(Continued)

*Primary Examiner* — Alfred J Wujciak
(74) *Attorney, Agent, or Firm* — John Maldjian; Maldjian Law Group LLC

(57) ABSTRACT

Disclosed is a counterbalance apparatus, and a method for counterbalancing using an apparatus, having a center of motion that is internal or external to the apparatus. The apparatus and method are adapted to support a payload, having a load vector applied in a direction of the vector or gravity, that is positioned distal to the center of motion. The apparatus includes a gimbal adapted to support the payload and allow for its rotational movement about the center of motion generating a load torque therefrom, and a resilient member adapted to engage the gimbal and supply a support torque to counterbalance the load torque. The method includes a step of supporting the payload with a gimbal adapted to allow rotational movement of the payload about the center of motion to generate a load torque therefrom, and
(Continued)

a step of configuring a resilient member to engage the gimbal and supply a support torque to counterbalance the load torque.

23 Claims, 12 Drawing Sheets

(51) Int. Cl.
*F16M 13/02* (2006.01)
*F16M 11/08* (2006.01)
*F16M 11/20* (2006.01)

(52) U.S. Cl.
CPC ....... *F16M 11/2057* (2013.01); *F16M 11/123* (2013.01); *F16M 2200/044* (2013.01)

(56) References Cited

U.S. PATENT DOCUMENTS

| | | | |
|---|---|---|---|
| 3,916,967 A * | 11/1975 | Carlisle | A47C 31/10 150/154 |
| 4,166,602 A * | 9/1979 | Nilsen | A61B 6/447 248/280.11 |
| 5,025,359 A * | 6/1991 | Saluja | F21V 21/28 248/325 |
| 6,206,832 B1 | 3/2001 | Downey et al. | |
| 8,444,543 B2 | 5/2013 | Fenster et al. | |
| 8,788,019 B2 | 7/2014 | Downey et al. | |
| 8,899,125 B2 | 12/2014 | Bax et al. | |
| 10,052,083 B2 | 8/2018 | Barker et al. | |
| 10,066,782 B2 | 9/2018 | Bax et al. | |
| 2004/0035243 A1 | 2/2004 | Duval | |
| 2007/0080275 A1* | 4/2007 | Stachowski | A61B 8/00 248/323 |
| 2007/0152115 A1* | 7/2007 | Chou | F16M 11/242 248/181.1 |
| 2008/0004481 A1 | 1/2008 | Bax et al. | |
| 2009/0234369 A1 | 9/2009 | Bax et al. | |
| 2010/0301179 A1 | 12/2010 | Brown | |
| 2010/0327129 A1* | 12/2010 | Chen | F16M 11/14 248/121 |
| 2011/0155866 A1 | 6/2011 | Brown et al. | |
| 2011/0277576 A1 | 11/2011 | Cooper | |
| 2012/0049035 A1 | 3/2012 | Black et al. | |
| 2014/0121675 A1 | 5/2014 | Bax et al. | |
| 2014/0135790 A1 | 5/2014 | Fenster et al. | |
| 2015/0053829 A1* | 2/2015 | Lu | F16M 13/022 248/123.11 |
| 2015/0168179 A1 | 6/2015 | Bax et al. | |
| 2016/0346940 A1 | 12/2016 | Bax et al. | |
| 2018/0051850 A1 | 2/2018 | Bax et al. | |
| 2018/0058529 A1 | 3/2018 | Bax et al. | |
| 2018/0112817 A1 | 4/2018 | Bax et al. | |
| 2018/0161114 A1 | 6/2018 | Bax et al. | |
| 2018/0243048 A1 | 8/2018 | Shan et al. | |

OTHER PUBLICATIONS

Beth W. Orenstein "Scanning in Pain—Sonographers Seek Relief From Job-Related Hazard" Radiology Today (2009): vol. 10 No. 18 p. 24 (2 pages total).

International Preliminary Report on Patentability dated Oct. 3, 2017 issued in connection with corresponding International Application No. PCT/CA2015/000204 (5 pages total).

International Search Report and Written Opinion dated Dec. 11, 2015 issued in connection with corresponding International Application No. PCT/CA2015/000204 (7 pages total).

* cited by examiner

COUNTERBALANCING APPARATUS FOR GIMBAL JOINTS AND/OR A METHOD FOR COUNTERBALANCING A LOAD ON A GIMBAL JOINT

CROSS-REFERENCE TO RELATED APPLICATIONS

This application is a § 371 national phase of International Application No. PCT/CA2015/000204, filed on Mar. 31, 2015, which application is incorporated by reference herein.

FIELD OF THE INVENTION

The present invention relates to a counterbalancing apparatus for gimbal joints and/or method for counterbalancing a load on a gimbal joint, and more particularly to a counterbalancing apparatus for gimbal joints comprising a single resilient member and/or a method for counterbalancing a load on a gimbal joint comprising a single resilient member.

BACKGROUND OF THE INVENTION

Many scientific, medical and industrial tasks involve the deployment of objects or instruments, which may need to be held aloft and manipulated in space for extended periods of time, resulting in repetitive stress to the user. The resulting repetitive stresses are known to be a cause of work-related trauma.

For example, work-related musculoskeletal disorders have been identified as a widespread problem amongst diagnostic medical sonographers and vascular technologists. In 2006, approximately 46,000 sonographer and vascular technologist job positions existed in the United States. A representative survey reported nearly 90% of sonographers and vascular technologists complete ultrasound scans while in some form of pain. Aggravating factors for pain during procedures was reported by sonographers to include sustained and repeated twisting of the neck and body, sustained arm abduction and application of pressure on the ultrasound transducer.

In a further example, poor ergonomics within industrial settings may also adversely affect the productivity and the health and safety of workers. Heavy tools or parts may require maneuvering in repetitive or awkward motions by workers within industrial settings. Workers may also be required to maintain fixed poses for extended periods of time. To improve worker ergonomics, devices have been developed to counterbalance tools or parts. These devices counteract the force of gravity to simulate the tool floating in air and improve worker ergonomics.

In the field of diagnostic medical sonography and vascular technology, for example, previous counterbalancing arms may have used high torque motors to counterbalance the load weight creating potential harm for a patient. For example, in the event of a malfunction, the motors may potentially drive the arm into the patient with a minimum force of twice the weight of the arm. In the event of a power failure, a traditional arm may lose its pose and slump under its own weight as the motors can no longer counterbalance the weight. While brakes may have been applied to prevent traditional arms from slumping in a power failure, the traditional arm may become fully locked (i.e., un-adjustable) until power is restored.

Prior attempts, if any, to solve problems associated with prior art devices and/or methods may have been unsuccessful and/or had one or more disadvantages associated with them. Prior art devices and/or methods have been ill-suited to solve the stated problems and/or the shortcomings which have been associated with them.

The zeroG™ system marketed by Equipois Inc. (Manchester, N.H.) is disclosed in U.S. Patent Application numbers 2011/0155866 and 2012/0049035 and includes a gimbal joint wrist mounted onto an arm consisting of two counterbalanced parallelogram segments. The zeroG™ system may be used to counterbalance tools in industrial settings to improve worker ergonomics.

Persons of skill in the art may understand that gimbal joints have a center of motion which is at the intersection point of all of the gimbal axes of rotation. The center of motion may be located at a point either within or outside the gimbal joints. If the center of motion is outside of the joints, it is known as a remote center of motion (RCM). The advantages of an RCM over an internal center of motion may be that the center of motion is not located in a volume occupied by the gimbal joints themselves. Accordingly, payloads or tools can be positioned at the RCM. If the center of mass of a payload (PCM) is positioned at the RCM, the payload will generate no net torque on the gimbal joint and will be counterbalanced without any intervention.

Notably, the gimbal joints used in the zeroG™ system are only counterbalanced when the payload or tool is mounted at center of rotation, which may constrain the positioning of a payload or tool relative to the wrist joint. More specifically, for apparatuses like the zeroG™ system, the PCM must be positioned at the RCM of the gimbal joint to achieve a counterbalance. If the PCM does not correspond with the RCM, the payload will not maintain its orientation when released by the operator and will slump. Requiring the PCM to correspond with the RCM, however, can be disadvantageous for certain applications. For instance, in many medical applications, the RCM is typically positioned on or inside of the patient in order to constrain a tool to a desired motion. If, however, the RCM is at the PCM then it cannot be positioned on or inside of the patient. In such a situation, the gimbals of the zeroG™ system would require relatively large arm linkages in order to produce an RCM capable of accommodating the tool or payload size.

Thus, there is a need for an improved counterbalancing apparatus for gimbal joints that preferably does not constrain positioning of loads, may produce either an internal center of motion or RCM, provides for the counterbalancing of payloads that are positioned away from the RCM, and is compact and lightweight in design. What is needed is a counterbalance apparatus and/or method that overcomes one or more of the limitations associated with the prior art. It may be advantageous to provide an apparatus and/or method which allow the user to manipulate a payload with minimal effort.

It is an object of the present invention to obviate or mitigate one or more of the aforementioned disadvantages and/or shortcomings associated with the prior art, to provide one of the aforementioned needs or advantages, and/or to achieve one or more of the aforementioned objectives of the invention.

SUMMARY OF THE INVENTION

According to an aspect of one preferred embodiment of the invention, there is disclosed a counterbalance apparatus, having a center of motion, for supporting a payload distal to the center of motion and having a load vector applied in a direction of the vector of gravity. The apparatus may include a gimbal and a resilient member. The gimbal may be adapted to support the payload and allow rotational movement of the payload about the center of motion and has a load torque generated by the rotational movement of the payload. The resilient member may be adapted to engage the gimbal and supply a support torque to counterbalance the load torque.

According to an aspect of one preferred embodiment of the invention, the counterbalance apparatus may preferably, but need not necessarily, have three gimbals.

According to an aspect of one preferred embodiment of the invention, the counterbalance apparatus may preferably, but need not necessarily, have two gimbals.

According to an aspect of one preferred embodiment of the invention, the gimbals may preferably, but need not necessarily, be mounted orthogonally.

According to an aspect of one preferred embodiment of the invention, the center of motion may preferably, but need not necessarily, be internal to the apparatus.

According to an aspect of one preferred embodiment of the invention, the center of motion may preferably, but need not necessarily, be external to the apparatus.

According to an aspect of one preferred embodiment of the invention, the resilient member may preferably, but need not necessarily, be adapted to produce an extension force.

According to an aspect of one preferred embodiment of the invention, the resilient member may preferably, but need not necessarily, be adapted to produce a compression force.

According to an aspect of one preferred embodiment of the invention, the resilient member may preferably, but need not necessarily, be a spring.

According to an aspect of one preferred embodiment of the invention, the spring may preferably, but need not necessarily, approximate a zero-length spring.

According to an aspect of one preferred embodiment of the invention, the spring may preferably, but need not necessarily, be a zero-length spring.

According to an aspect of one preferred embodiment of the invention, the counterbalance apparatus may preferably, but need not necessarily, further include a preload member to engage the resilient member to alter a magnitude of the support torque.

According to an aspect of one preferred embodiment of the invention, the counterbalance apparatus may preferably, but need not necessarily, further include counterbalance adjust blocks to alter the magnitude of the support torque.

According to an aspect of one preferred embodiment of the invention, the rotation of the counterbalance apparatus about a roll axis may preferably, but need not necessarily, be about less than or equal to 180 degrees inwards and about less than or equal to 180 degrees outwards.

According to an aspect of one preferred embodiment of the invention, the rotation of the counterbalance apparatus about a pitch axis may preferably, but need not necessarily, be about plus or minus 180 degrees.

According to an aspect of one preferred embodiment of the invention, the support torque may preferably, but need not necessarily, counterbalance the load torque with at least two degrees of freedom.

According to an aspect of one preferred embodiment of the invention, the counterbalance apparatus may preferably, but need not necessarily, further include a ball joint to facilitate engagement of the gimbal by the resilient member.

According to an aspect of one preferred embodiment of the invention, there is disclosed a method for supporting a payload using a counterbalance apparatus, having a center of motion, the payload distal to the center of motion and having a load vector applied in a direction of the vector of gravity. The method includes step (a) and step (b). In step (a), the payload is attached to a gimbal adapted to allow rotational movement of the payload about the center of motion, the rotational movement of the payload generating a load torque. In step (b), a resilient member is configured to engage the gimbal and supply a support torque to counterbalance the load torque.

According to an aspect of one preferred embodiment of the invention, in step (a), the gimbal may preferably, but need not necessarily, include three gimbals.

According to an aspect of one preferred embodiment of the invention, in step (a), the gimbal may preferably, but need not necessarily, include two gimbals.

According to an aspect of one preferred embodiment of the invention, in step (a), the gimbals may preferably, but need not necessarily, be mounted orthogonally.

According to an aspect of one preferred embodiment of the invention, in step (a), the center of motion is preferably, but need not necessarily, internal to the apparatus.

According to an aspect of one preferred embodiment of the invention, in step (a), the center of motion is preferably, but need not necessarily, external to the apparatus.

According to an aspect of one preferred embodiment of the invention, in step (b), the resilient member is preferably, but need not necessarily, used to produce an extension force.

According to an aspect of one preferred embodiment of the invention, in step (b), the resilient member is preferably, but need not necessarily, used to produce a compression force.

According to an aspect of one preferred embodiment of the invention, in step (b), the resilient member may preferably, but need not necessarily, be a spring.

According to an aspect of one preferred embodiment of the invention, in step (b), the spring may preferably, but need not necessarily, approximate a zero-length spring.

According to an aspect of one preferred embodiment of the invention, in step (b), the spring may preferably, but need not necessarily, be a zero-length spring.

According to an aspect of one preferred embodiment of the invention, before steps (a) through (b), a preload member may preferably, but need not necessarily, be used to engage the resilient member to alter a magnitude of the support torque.

According to an aspect of one preferred embodiment of the invention, before steps (a) through (b), counterbalance adjust blocks may preferably, but need not necessarily, be used to alter the magnitude of the support torque.

According to an aspect of one preferred embodiment of the invention, the method may preferably, but need not necessarily, also include a step of rotating the apparatus about a roll axis about less than or equal to 180 degrees inwards and about less than or equal to 180 degrees outwards.

According to an aspect of one preferred embodiment of the invention, the method may preferably, but need not necessarily, also include a step of rotating the apparatus about a pitch axis about plus or minus 180 degrees.

According to an aspect of one preferred embodiment of the invention, in step (b), the support torque may preferably, but need not necessarily, counterbalance the load torque with two degrees of freedom.

According to an aspect of one preferred embodiment of the invention, before steps (a) through (b), a ball joint may preferably, but need not necessarily, be used to facilitate engagement of the gimbal by the resilient member.

Other advantages, features and characteristics of the present invention, as well as methods of operation and functions of the related elements of the apparatus and method, and the combination of steps, parts and economies of manufacture, will become more apparent upon consideration of the following detailed description and the appended claims with reference to the accompanying drawings, the latter of which are briefly described herein below.

BRIEF DESCRIPTION OF THE DRAWINGS

The novel features which are believed to be characteristic of the apparatus and method according to the present invention, as to their structure, organization, use, and method of operation, together with further objectives and advantages thereof, will be better understood from the following drawings in which presently preferred embodiments of the invention will now be illustrated by way of example. It is expressly understood, however, that the drawings are for the purpose of illustration and description only, and are not intended as a definition of the limits of the invention. In the accompanying drawings.

DETAILED DESCRIPTION OF THE PREFERRED EMBODIMENTS

Figure 1:
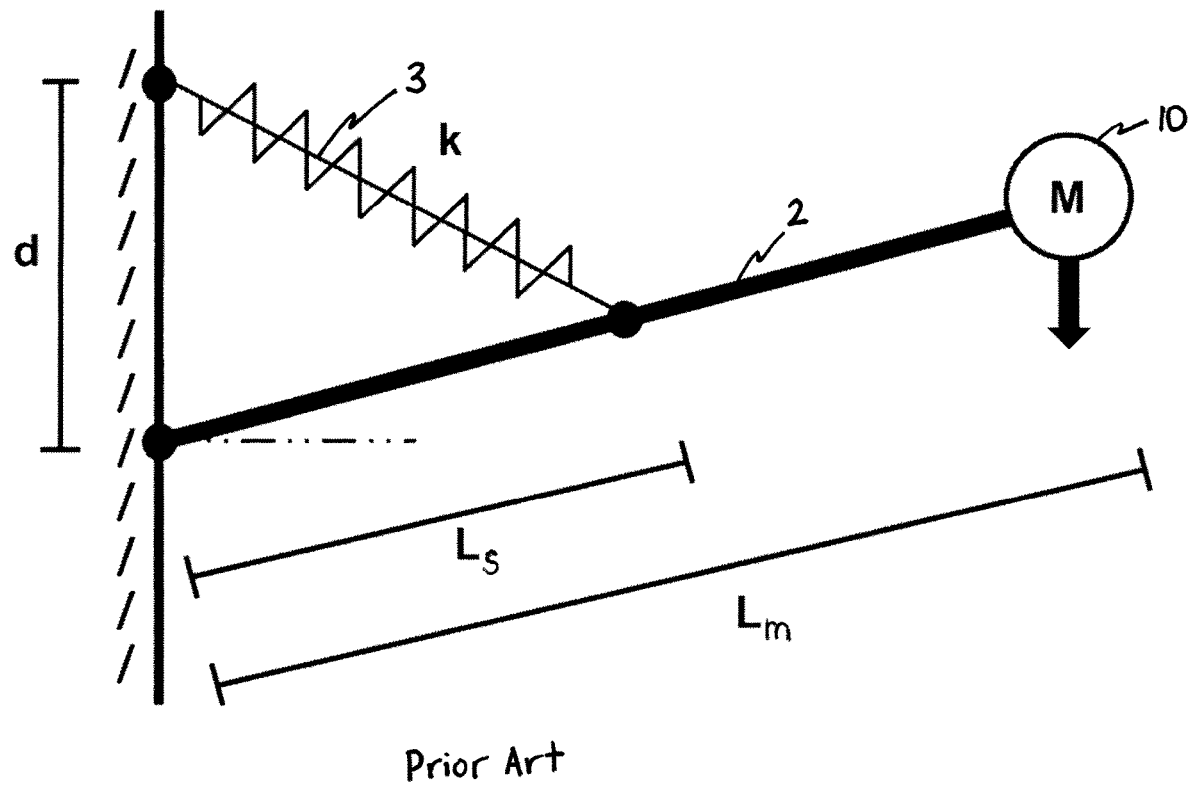
FIG. 1 is a schematic diagram of a single spring counterbalance of the prior art.

The description that follows, and the embodiments described therein, is provided by way of illustration of an example, or examples, of particular embodiments of the principles of the present invention. These examples are provided for the purposes of explanation, and not of limitation, of those principles and of the invention. In the description, like parts are marked throughout the specification and the drawings with the same respective reference numerals. The drawings are not necessarily to scale and in some instances proportions may have been exaggerated in order to more clearly depict certain embodiments and features of the invention.

In this disclosure, a number of terms and abbreviations are used. The following definitions of such terms and abbreviations are provided.

As used herein, a person skilled in the relevant art may generally understand the term "comprising" to generally mean the presence of the stated features, integers, steps, or components as referred to in the claims, but that it does not preclude the presence or addition of one or more other features, integers, steps, components or groups thereof.

In the description and drawings herein, and unless noted otherwise, the terms "vertical", "lateral" and "horizontal", are generally references to a Cartesian co-ordinate system in which the vertical direction generally extends in an "up and down" orientation from bottom to top (y-axis) while the lateral direction generally extends in a "left to right" or "side to side" orientation (x-axis). In addition, the horizontal direction extends in a "front to back" orientation and can extend in an orientation that may extend out from or into the page (z-axis). Unless indicated otherwise, the force or vector of gravity acts parallel to the y-axis (e.g., the vertical direction) in a general downward manner.

As used herein, a person skilled in the relevant art would understand that a "gimbal" is a pivoted support that allows the rotation of an object about a single axis. Gimbals may preferably, but need not necessarily, be mounted as sets of two or three. A set of three gimbals, for example, one mounted on the other with orthogonal pivot axes, may be used to allow an object mounted on the innermost gimbal to remain independent of the rotation of its support.

As used in the specification, there may be defined three axes of rotation with respect to the apparatus. Each axis of this coordinate system is perpendicular to the other two axes. For example, the pitch axis is perpendicular to the yaw axis and the roll axis. A roll motion or "roll" is a rotation of the apparatus along the z-axis. A yaw motion or "yaw" is a rotation of the apparatus along the y-axis. A pitch motion or "pitch" is a rotational movement of the apparatus along the x-axis.

As used herein, a person skilled in the relevant art would understand that a "resilient member" may comprise one or more of any of the following elastic, pneumatic, gas spring, constant force spring motor, or other device adapted to store or exert mechanical energy, generate force and/or that is back-drivable (e.g., force applied to an output can move an input). In a preferred embodiment, a resilient member may comprise a spring and in a more preferred embodiment, may comprise a compression or extension spring. While springs may preferably be used in the figures, persons skilled in the art will understand that any force generating device may be used in the system described herein. A force generating device refers to any structure or device which provides resistance to compressive or tensile forces in response to linear deflection imposed thereon. More specifically, any structure or device that exhibits resistance to linear compression or tension along a longitudinal axis thereof may be useful as a force generating device. Thus, a force generating device includes a longitudinal axis along which linear forces shall be imposed as a result of rotational movement of a mechanical arm. The force generating device interacts with a cam to convert rotational movement of the arm into linear deflection of the force generating device. An example of a force generating device is a spring-like device. A spring-like device is any device or structure that acts like a compression or tension spring in providing resistance to a linear compression and/or tension along a longitudinal axis. An example of a spring-like device is a unit of rubber or other resilient material, or a pneumatic pressurized cylinder any one of which may be used in an equivalent manner to a compression or tension spring by providing resistance to a linear force along a longitudinal axis. Another example of a spring-like device is a spring, such as a compression spring or a tension spring. Compression springs are an example of a low cost force generating device that may be utilized to provide a simplified arrangement within the counterbalance assembly. A compression spring includes a longitudinal axis along which linear compressive forces may be imposed as a result of rotational movement of a mechanical arm. Examples of compression springs include relatively standard die springs as commonly available in the industry. The exact number and size of such springs used in the counterbalance assembly described herein can vary depending upon the counterbalance torque desired, the size of the robotic arm involved, and the like, as will be recognized by the skilled person. The force generating device may be adjustable such that the resistive force provided by the force generating device may be increased or decreased to allow for variation in mechanical arms.

As used herein, persons skilled in the relevant art would understand that a torque or moment is the tendency of a force to rotate an object about an axis or pivot.

Lastly, as used herein, "zero length spring" is a term for a mathematical model of a spring that would exert zero force if it had zero length.

There is a need in the art for apparatus and methods for exerting a force (e.g., to counteract the torque produced by a payload or the force of gravity) in order to reduce the physical effort exerted by users in various settings, including, but not limited to, medical professionals in performing medical examinations (e.g., ultrasound examinations). More particularly, there is a need in the art for an apparatus that can counterbalance a load connected to gimbal joints.

An aspect of the present invention thereby preferably provides systems and methods to reduce the physical strain which may be experienced by users, including, but not limited to, medical practitioners who perform ultrasound examinations and similar medical procedures. It will be understood, however, that the present invention may be used to assist the performance of various tasks found in other settings, including, but not limited to, industrial environments.

In order that the invention may be more fully understood, it will now be described, by way of example, with reference to the accompanying drawings in which FIG. 1 through FIG. 7 illustrate embodiments of the present invention.

Persons skilled in the art may appreciate that the concept of the single spring counterbalance is well known in the art, for example, as discussed in Agrawal, A. et al., (2005), Design of gravity balancing leg orthosis using non-zero free length springs, *Mechanism and Machine Theory*, 40 (2005), 693-709, herein incorporated by reference. Referring now to FIG. 1 there is depicted a basic schematic of a single resilient member of the prior art, preferably, but need not necessarily, a spring, counterbalance applied to an arm 2, where:

M=Mass of the payload;
k=Constant of the spring;
$L_m$=Distance of payload center of mass to arm base;
$L_s$=Distance of spring arm attachment point to arm base; and
d=Distance of spring base attachment point to arm base.

The payload shown in FIG. 1 may be counterbalanced if, for example, a spring 3 of an appropriate spring constant, k, is selected. As may be disclosed by Agrawal et al., the spring constant, k, required for counterbalancing the mass of a payload 10 can be approximated by the equation:

$$k = \frac{MgL_m}{dL_s\left(1 - \frac{x_o}{\sqrt{d^2 + L_s^2}}\right)} \quad (1)$$

where $x_o$ is the free length of the spring 3. Equation (1) may be simplified for the special case of a zero-length spring. Persons skilled in the art may understand that a zero-length spring is a spring whose free length $x_o$=0 (i.e., the spring will exert zero force when its length is equal to zero). For a zero-length spring, equation (1) can be written as:

$$k = \frac{MgL_m}{dL_s} \quad (2)$$

Persons skilled in the art may appreciate that equation (1) is derived using what may be known as a Taylor series approximation and assumes that a non-zero length spring is used for counterbalancing the mass of the payload. As a result, a spring selected using equation (1) may not provide a perfect counterbalance for the payload. For a single link or arm, Agrawal et al. may have determined that a non-zero length spring selected using equation (1) may provide an incomplete force required to counterbalance the mass of a payload. On the other hand, equation (2) may preferably provide a spring that supplies 100% of the force required to counterbalance the mass of a payload. A zero-length spring selected by equation (2) may theoretically provide a perfect counterbalance for the mass of a payload. However, in practice, zero-length springs can be challenging to implement. In addition, the majority of off-the-shelf springs are non-zero length.

The selection of zero-length springs may be limited and may only be available at high cost. Significantly, however, non-zero length springs may be made to mimic or approximate the behavior of a zero length spring. That being said, persons of ordinary skill in the art may understand that in order to mimic or approximate a zero length spring with a non-zero length spring mechanisms which increase the complexity of the counterbalance may be required. Accordingly, while a non-zero length spring counterbalance may be less complicated to implement, it may provide an incomplete (or imperfect) counterbalance for the mass of a payload. On the other hand, while a zero length spring counterbalance may be more complicated to implement, it may provide a more complete (or perfect) counterbalance for the mass of a payload.

The apparatus of the present invention provides a single resilient member counterbalance preferably adapted for use with gimbal-type joints. The invention preferably, but need not necessarily, provides a novel method for counterbalancing payloads mounted onto gimbal joints. A zero length spring or a non-zero length spring may be used in the present invention for the counterbalance of a gimbal joint.

Figure 2A:
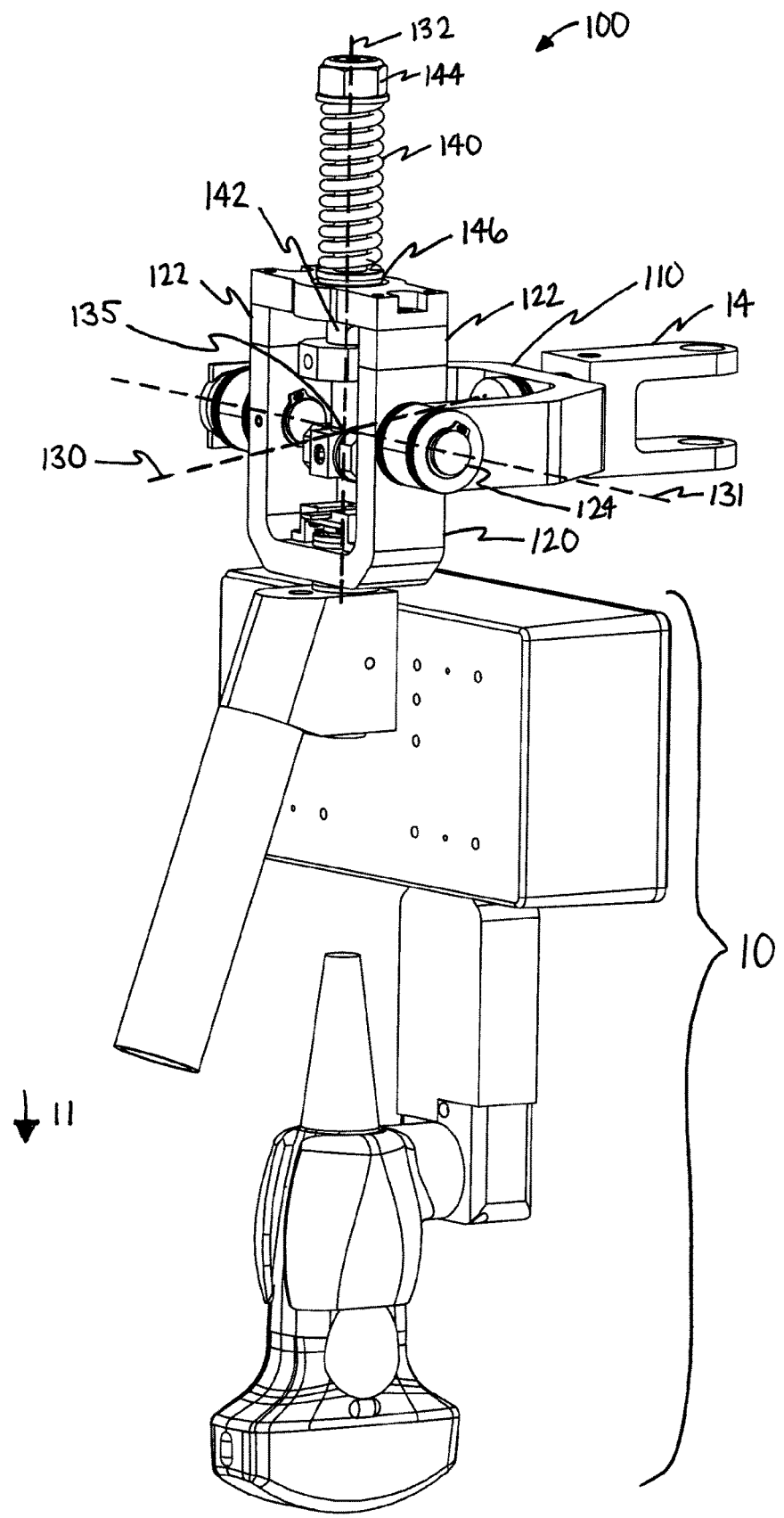
FIGS. 2A and 2B are perspectives view of an apparatus with a load and cross-sectioned, respectively.
Figure 2B:
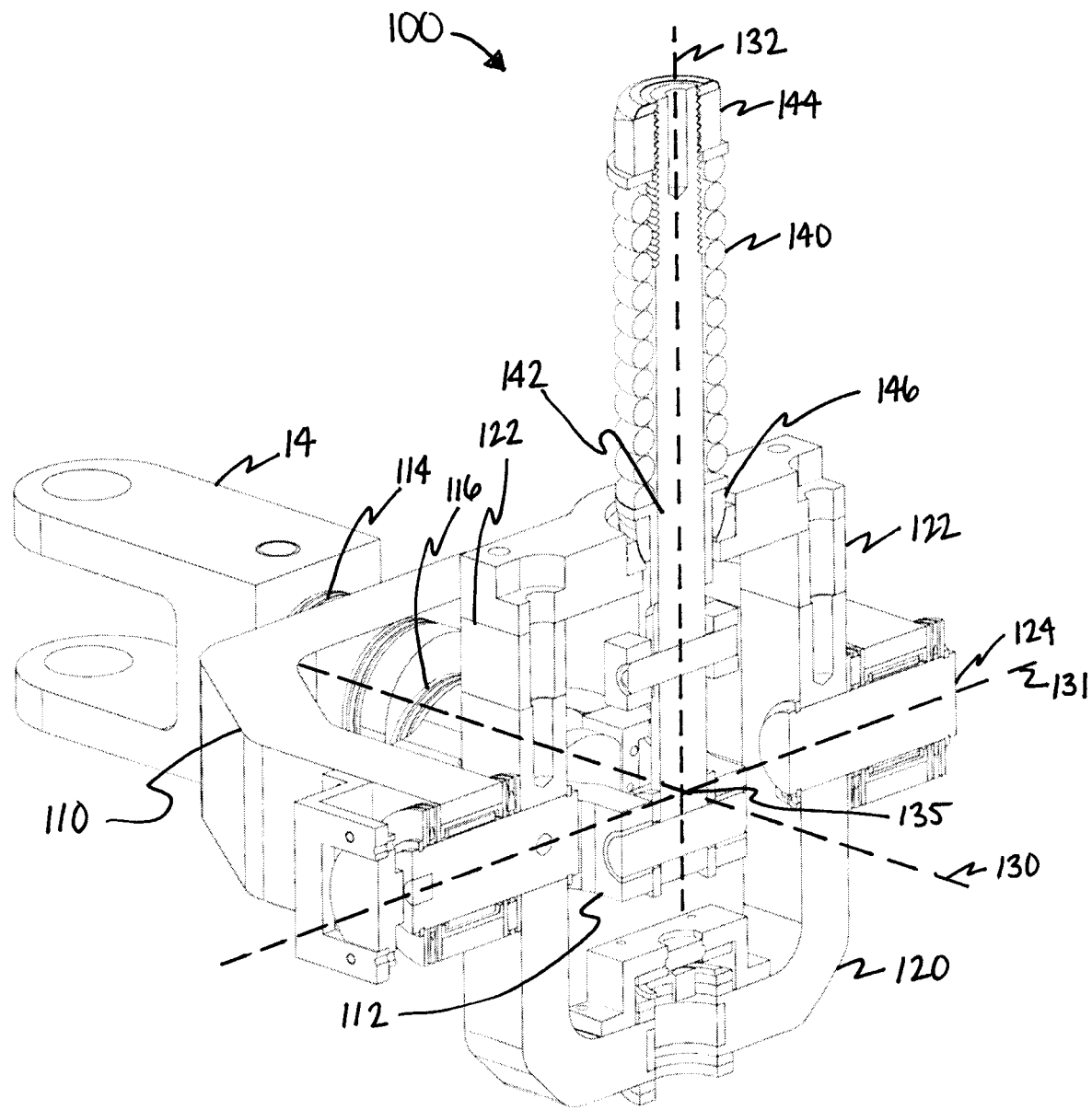

Referring to FIG. 2, there is provided a counterbalance apparatus 100 of the present invention including a counterbalanced gimbal wrist joint supporting a payload 10 with load vector 11, such as a three-dimension ultrasound imaging system. As depicted in FIGS. 2A and 2B, the payload 10 may consist of an ultrasound transducer, transducer mover and handle. The apparatus 100 preferably, but need not necessarily, contains a first spherical arm 110 pivotally connected to a base attachment bracket 14 at a first pivot 114 and a second spherical arm 120 pivotally connected to the first arm 110 at a second pivot 124, the first pivot 114 and the second pivot 124 forming two intersecting rotational axes, roll 130 and pitch 131, which may hereafter alternately be referenced as the first axis 130 and second axis 131. The point of intersection of the roll axis 130 and pitch axis 131 is the counterbalance point 135 or center of motion for the apparatus 100. A support post or other structure, for example, an armature 112, preferably projects from the first arm 110 at a support post pivot 116 and is rotatable about the first axis 130. The second arm 120 is preferably, but need not necessarily, adapted to engage the payload 10 at a load bearing end. The second arm 120 also preferably, but need not necessarily, comprises a thrust bearing ball joint 146 at a counterbalance end. A counterbalance post 142, having a first end and a second end, wherein the first end is pivotally attached to the support post 112, preferably but need not necessarily, at a point offset from the counterbalance point 135 and the second end projects through the ball joint 146 to define a third axis 132 (alternately referenced as the counterbalance axis 132). The counterbalance post 142 preferably comprises a preload member 144 at the second end. A resilient member 140 may preferably be mounted or captured on the counterbalance post 142 between the preload member 144 and the ball joint 146. The counterbalance resilient member 140 preferably counterbalances the payload 10 throughout the range of motion of the two rotational axes 130,131. The resilient member 140 preferably generates a counterbalance torque vector 102 (alternately hereafter referred to as the support torque 102, as best seen in FIGS. 5A, 5C, 6A, and 6C) is defined by the equations previously discussed. The counterbalance resilient member 140 is preferably, but need not necessarily, a non-zero length compression spring which has been integrated such that it mimics, or approximates, a zero length spring counterbalance as will be illustrated herein. The base (not shown) and base attachment bracket 14 may be used to attach the apparatus 100 onto the end of a mechanical arm (not shown). Also shown, but discussed with respect to FIG. 3, are counterbalance adjust blocks 122.

Figure 3:
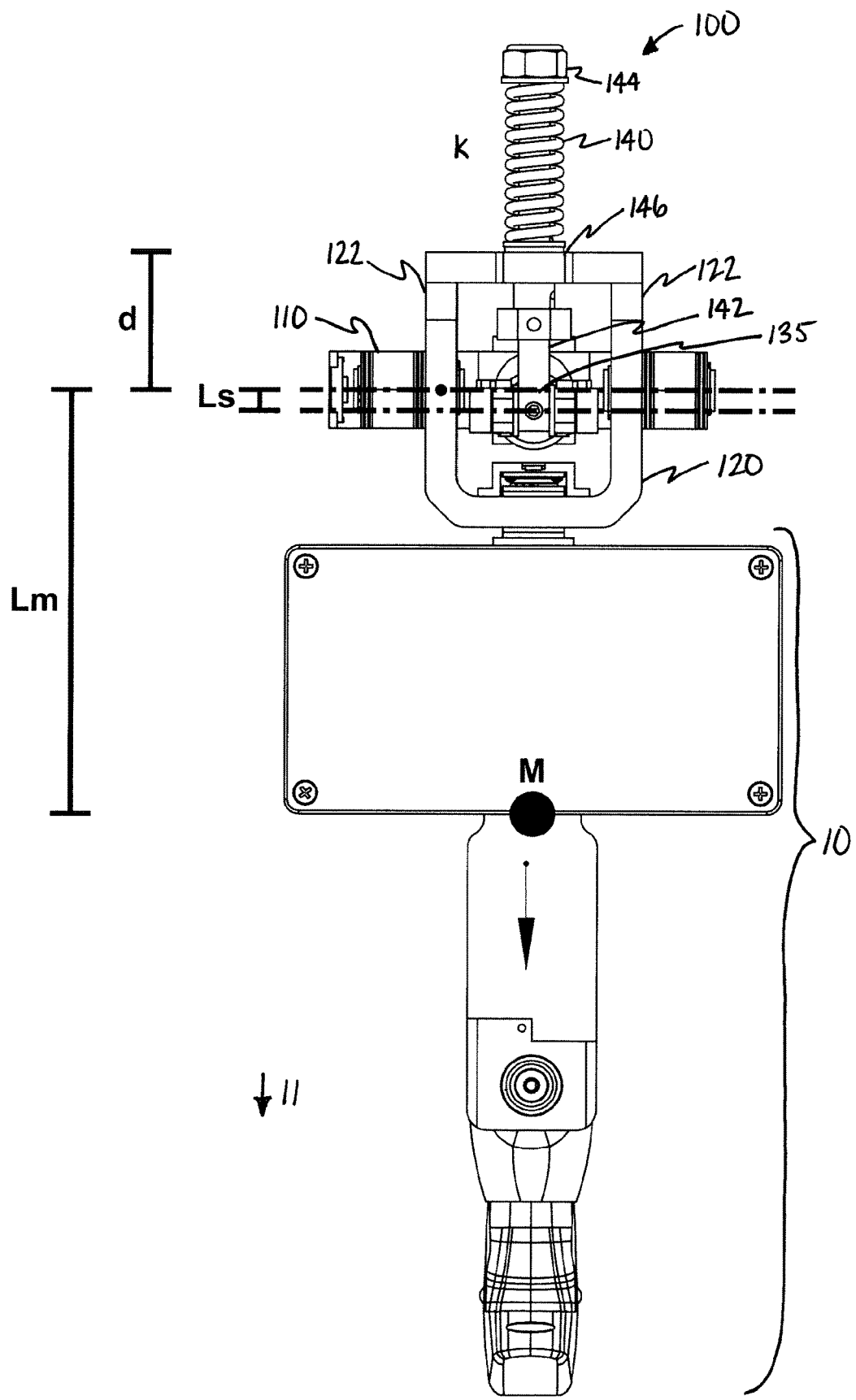
FIG. 3 is a front view of the apparatus of FIG. 2A.

FIG. 3 depicts the apparatus 100 with reference to the variables described in equation (2) above. In some embodiments, a resilient member 140 is preferably but need not necessarily selected to accommodate the load vector 11 of the payload 10, as the apparatus 100 has limited adjustability for accommodating payloads 10 having different load vectors 11 using a single resilient member 140. In preferable embodiments, the apparatus 100 may be adjusted to accommodate payloads 10 having different load vectors 11 by using counterbalance adjust blocks 122 situated in one of the spherical arms 110, 120. As depicted in FIG. 3, the blocks 122 are preferably installed in the second arm 120. Referring to equation (2), the addition or removal of the counterbalance adjust blocks 122 will modify the value of the variable "d" (e.g., the distance from the bearing joint 146 to the counterbalance point 135), which in turn, modifies a magnitude of the counterbalance torque 102 exerted by the apparatus 100. Persons skilled in the art will appreciate that counterbalance adjust blocks 122 of different sizes may be used to provide incremental changes to variable "d" and that blocks 122 that increase the value of "d" will increase the counterbalance capability of the apparatus 100 (i.e., the apparatus 100 will be capable of counterbalancing payloads 10 of increasing load vectors 11). Changing the counterbalance adjust blocks 122 may require partial disassembly of the apparatus 100. The counterbalance adjust blocks 122 are preferably, but need not necessarily, intended for supporting small changes in the load vector 11 of the payload 10 and may not be adaptable for accommodating large changes in the load vector 11 of the payload 10. Larger changes in the load vector 11 of the payload 10 may preferably, but need not necessarily, require the use of a resilient member 140 with a different capacity for supporting a payload 10 (e.g., a spring with a different spring constant, k).

Figure 4:
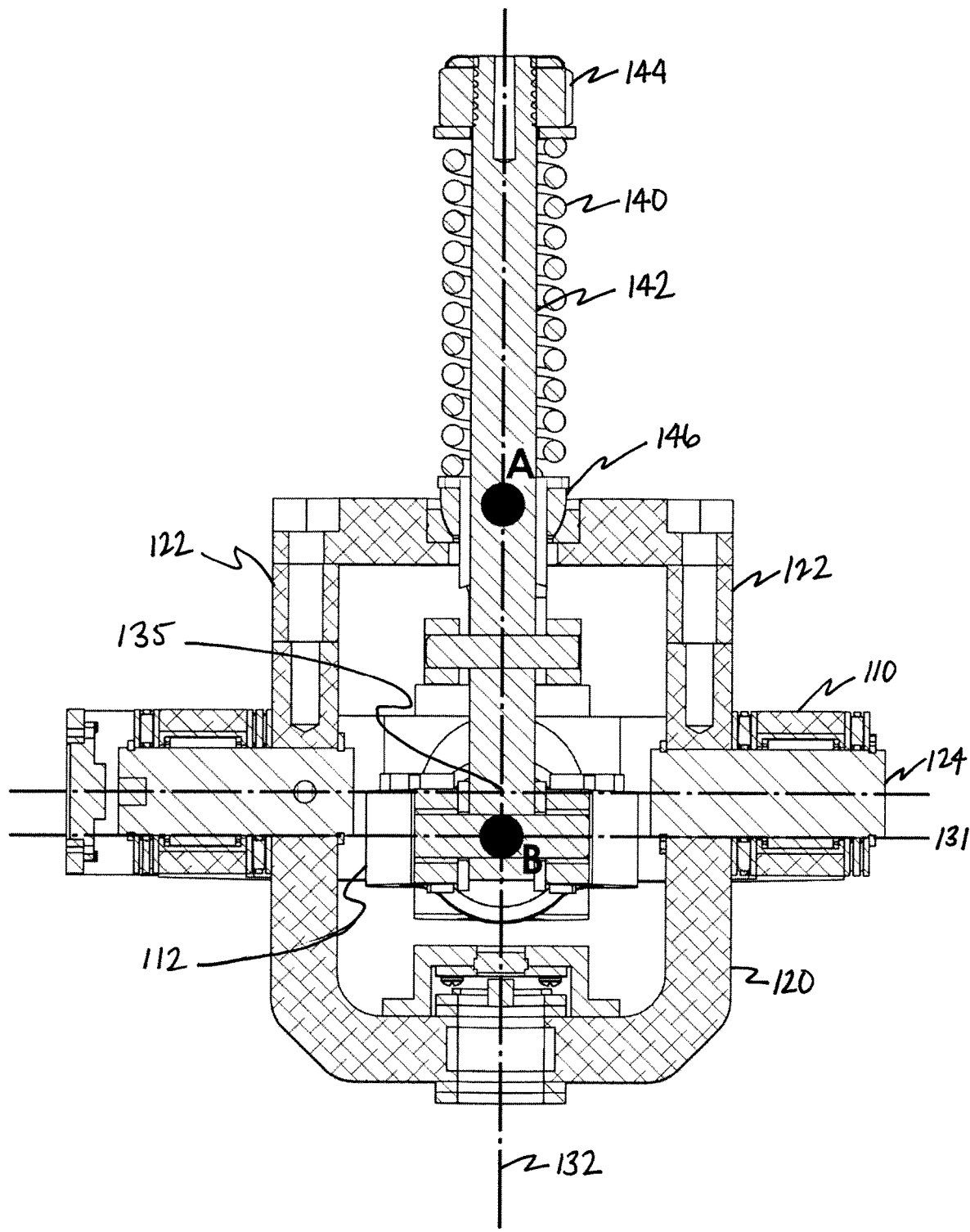
FIG. 4 is a front cross-sectional view of the apparatus of FIG. 2A (load not shown)

FIG. 4 provides a front cross-sectional view of the apparatus 100 (payload not shown). The apparatus 100 is preferably, but need not necessarily, adapted to achieve a zero-free length counterbalance from a non-zero length spring. The resilient member 140 is preferably, but need not necessarily, a compression spring captured by the counterbalance post 142. The spring 140 is preferably positioned between the preload member 144 and the thrust bearing ball joint 146. Those skilled in the art will understand that a thrust bearing is a rotary rolling-element bearing that preferably permits rotation between parts and is adapted to support a predominantly axial load. The preload member 144 is preferably, but need not necessarily, rigidly attached to the post 142. In an alternate preferred embodiment, the preload member 144 may threadably engage the post 142. Adjustment of the preload member 144 may preferably, but need not necessarily, alter the magnitude of the counterbalance torque 102 (as seen in FIGS. 5A, 5C, 6A and 6C) exerted by the resilient member 140. The post 142 is preferably, but need not necessarily, supported by the thrust bearing ball joint 146 and may pivotally be connected to the support post 112 of the first spherical arm 110 at the counterbalance point 135. As the apparatus 100 rotates about the two rotational axes (i.e., the roll axis 130 and the pitch axis 131), the post 142 preferably slides in the ball joint 146 causing the compression spring 140 to change in length. Persons skilled in the art will understand that the zero-force behavior of the apparatus 100 may be represented by a theoretical construct of an extension spring positioned between the bearing ball joint 146 at point "A" and a first end of the post 142 at point "B". The force exerted by the theoretical extension spring positioned between points "A" and "B" is preferably, but need not necessarily, equivalent to the magnitude of the torque 102 (as seen in FIGS. 5A, 5C, 6A and 6C) exerted by the resilient member 140 positioned between the preload member 144 and thrust bearing ball joint 146.

Figure 5A:
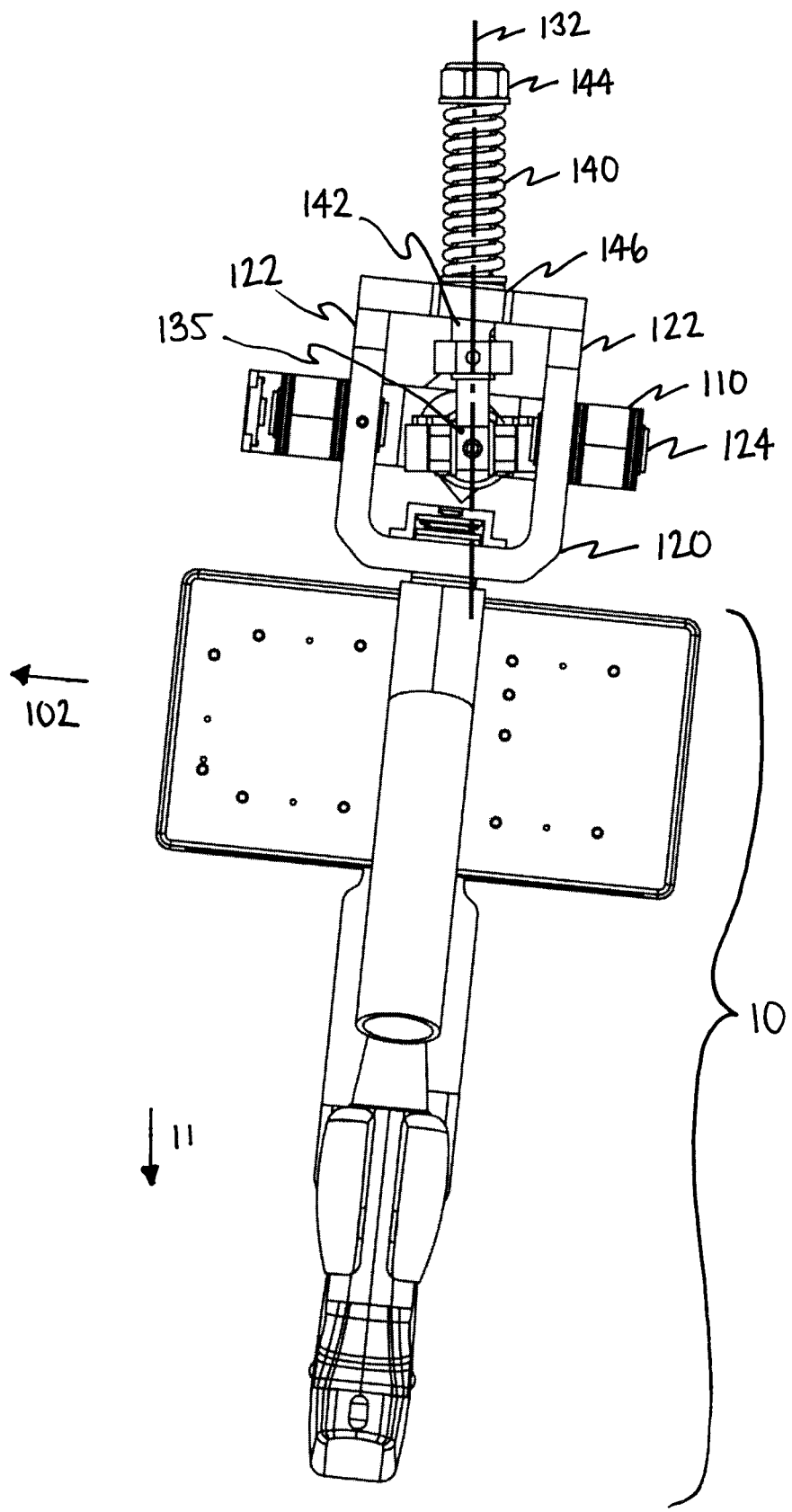
FIG. 5A, B, C are front views of the apparatus of FIG. 2 rotating about the roll axis.

As is best seen in FIGS. 5ABC and 6ABC, in operation, as the apparatus 100 is rotated about axes 130, 131, the post 142 preferably slides in the ball bearing joint 146 causing the resilient member 140 to compress or relax to create a torque 102 in a direction of the z-axis. In addition, as the post 142 slides, the points "A" and "B" (as seen in FIG. 4) will move towards and away from one another causing the theoretical extension spring to extend or relax. Persons skilled in the art will understand that for a zero length counterbalance to be achieved, if points "A" and "B" were to become coincident the theoretical extension spring would need to exert zero force. The resilient member 140 may preferably, but need not necessarily, be preloaded by adjusting the position of the preload member 144 (threadably engaged) such that that it will be unloaded (or relaxed) and under no compression when points "A" and "B" are coincident. Accordingly, a zero length counterbalance may preferably be achieved by preloading the compression spring 140 a predetermined (appropriate) distance. The (predetermined) distance required for preload is equal to the distance between points "A" and "B" when the apparatus 100 is at its home position (i.e., the payload 10, for example an ultrasound transducer, is perfectly upright with no tilt on either axis 130, 131 and zero counterbalance torque is required).

As shown in FIGS. 5ABC and 6ABC, there is depicted the motion of the apparatus 100, supporting a payload 10 with a load vector 11, having two rotational degrees of freedom. The two rotational axes are preferably, but need not necessarily, independent of each other and can be adjusted individually.

Figure 5B:
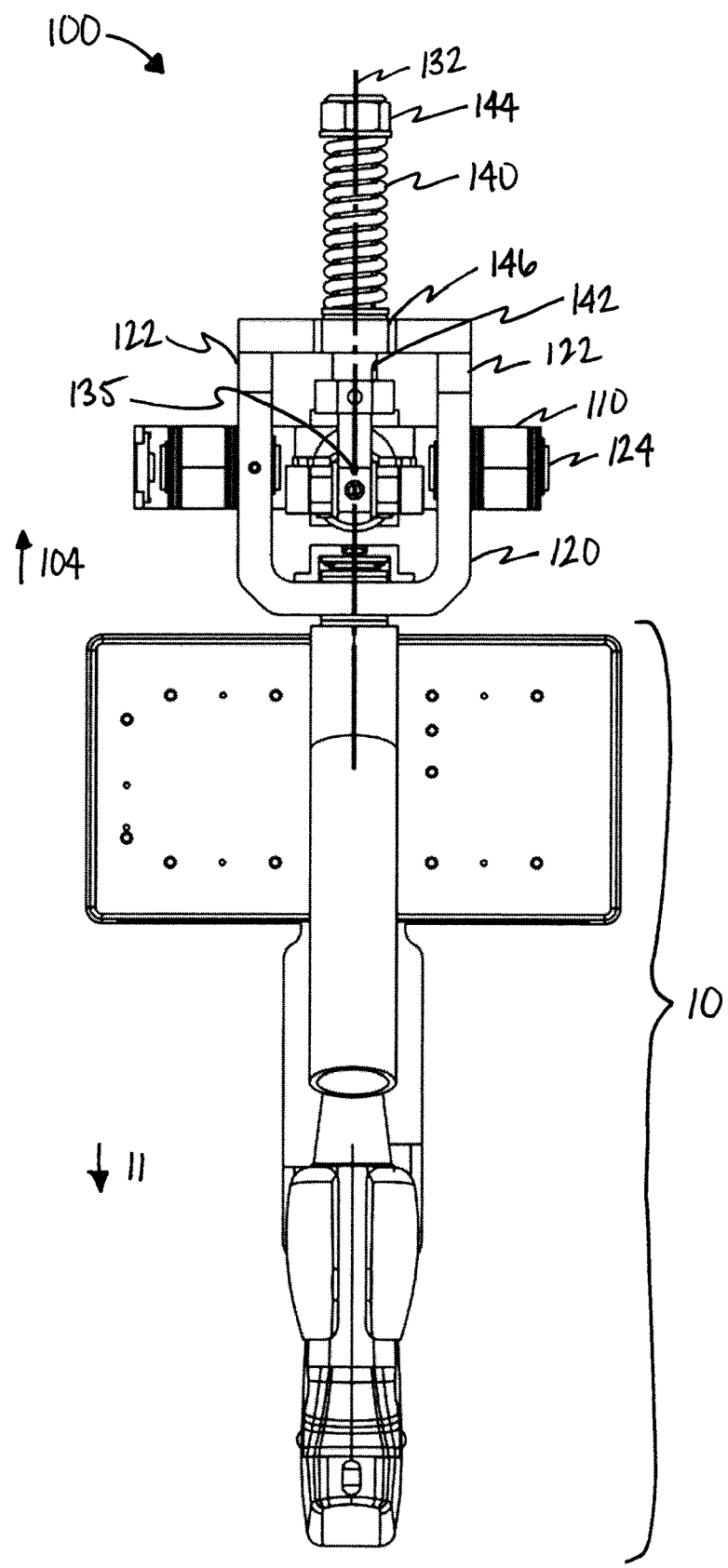
Figure 5C:
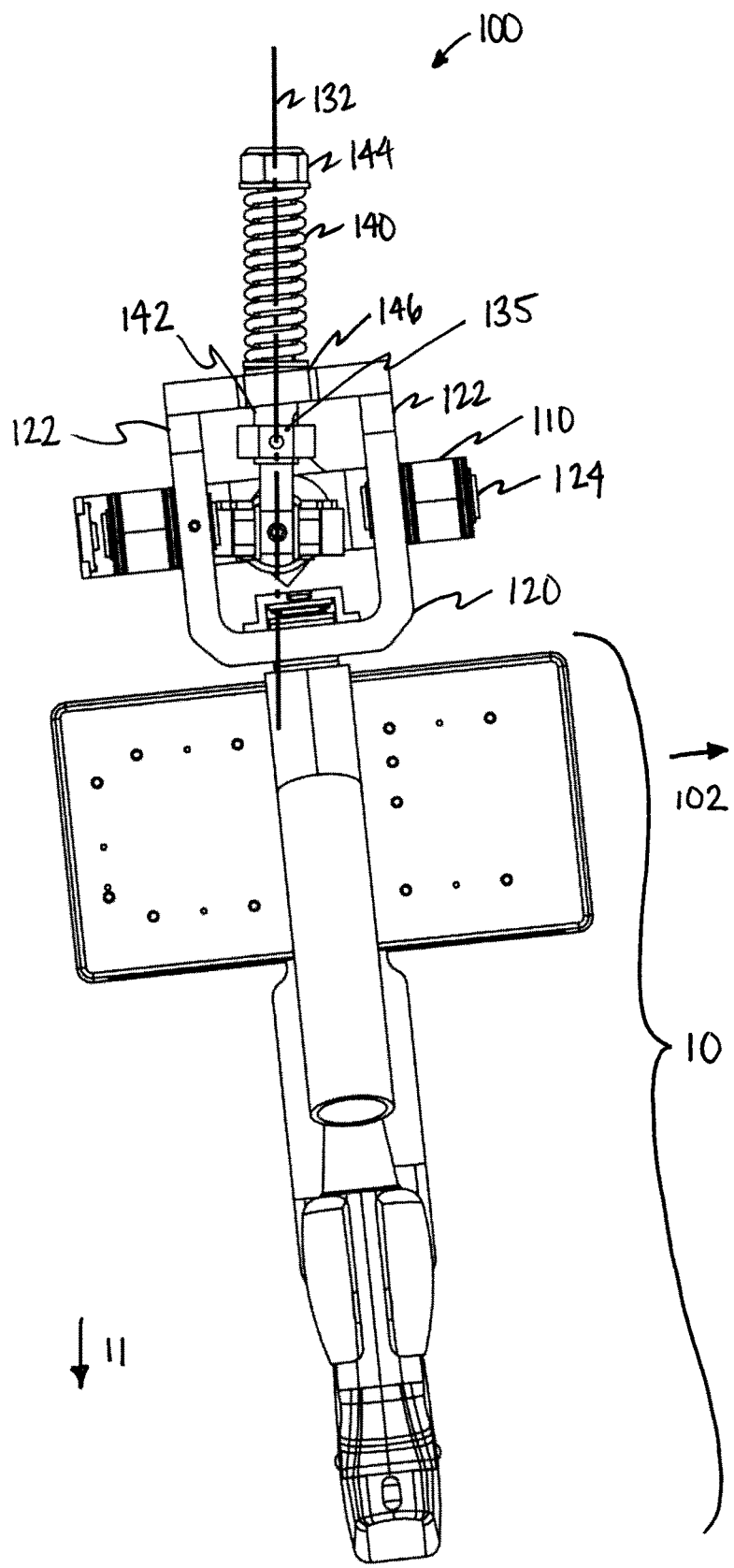

Referring to FIG. 5ABC, there is depicted the apparatus 100 pivoting about the roll axis (i.e., first axis) from left to right across the page. As shown in FIGS. 5A and 5C, rotation of the apparatus 100 to the left or right of the page about the roll axis 130 (not shown) will cause the counterbalance axis 132 to diverge from the counterbalance point 135 creating a torque or moment to produce a counterbalancing torque 102 in a direction of the z-axis and having a given magnitude to counterbalance the torque produced by the load vector 11 associated with the payload 10. FIG. 5B depicts the apparatus 100 in position such that the counterbalance axis 132 is aligned with the counterbalance point 135. While no torque is produced by the resilient member 140 or the payload 10, the member 140 produces a net force 104 having a given magnitude to support the load vector 11 associated with the payload 10.

Figure 6A:
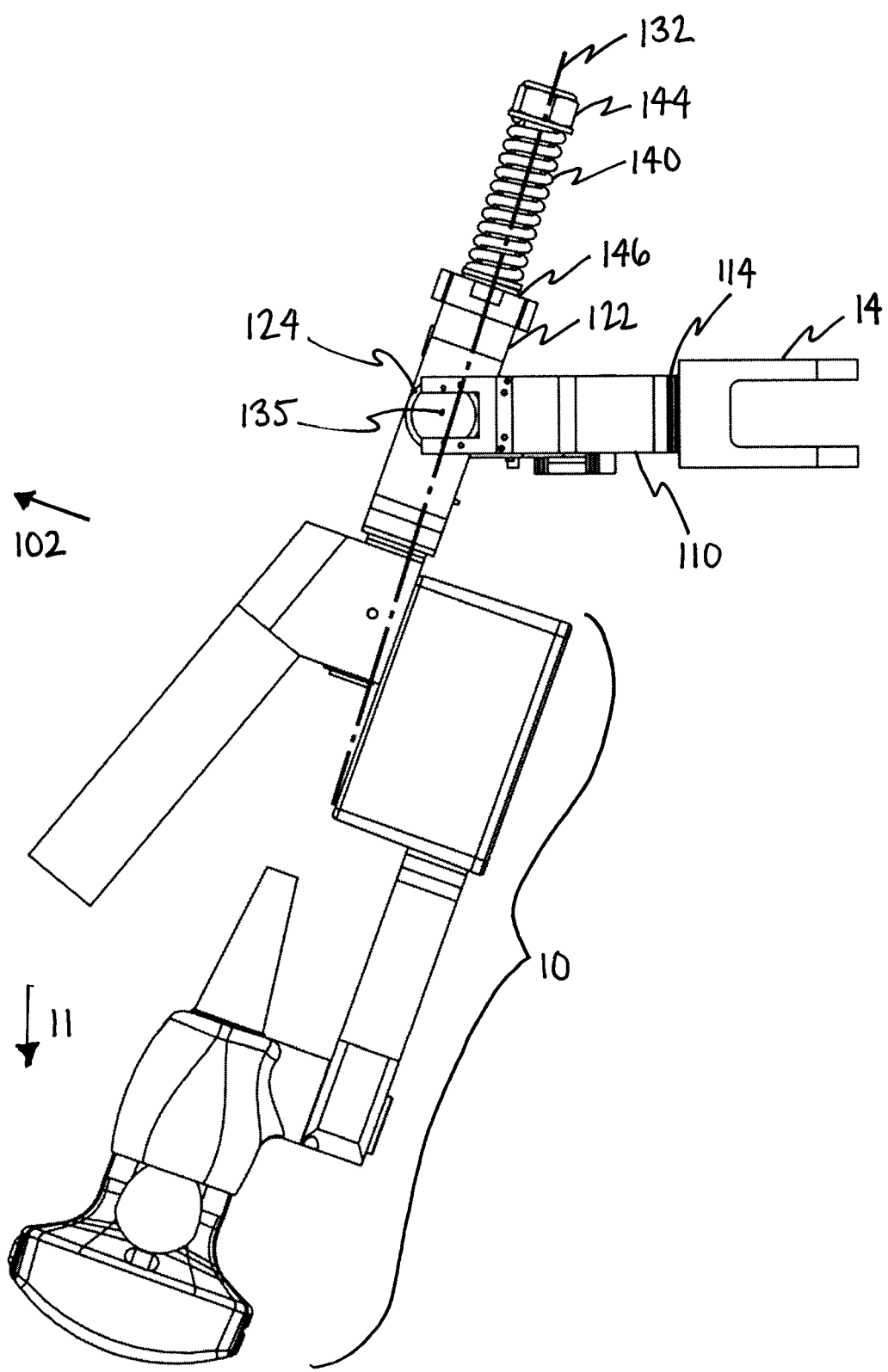
FIG. 6A, B, C are side views of the apparatus of FIG. 2 rotating about the pitch axis.
Figure 6B:
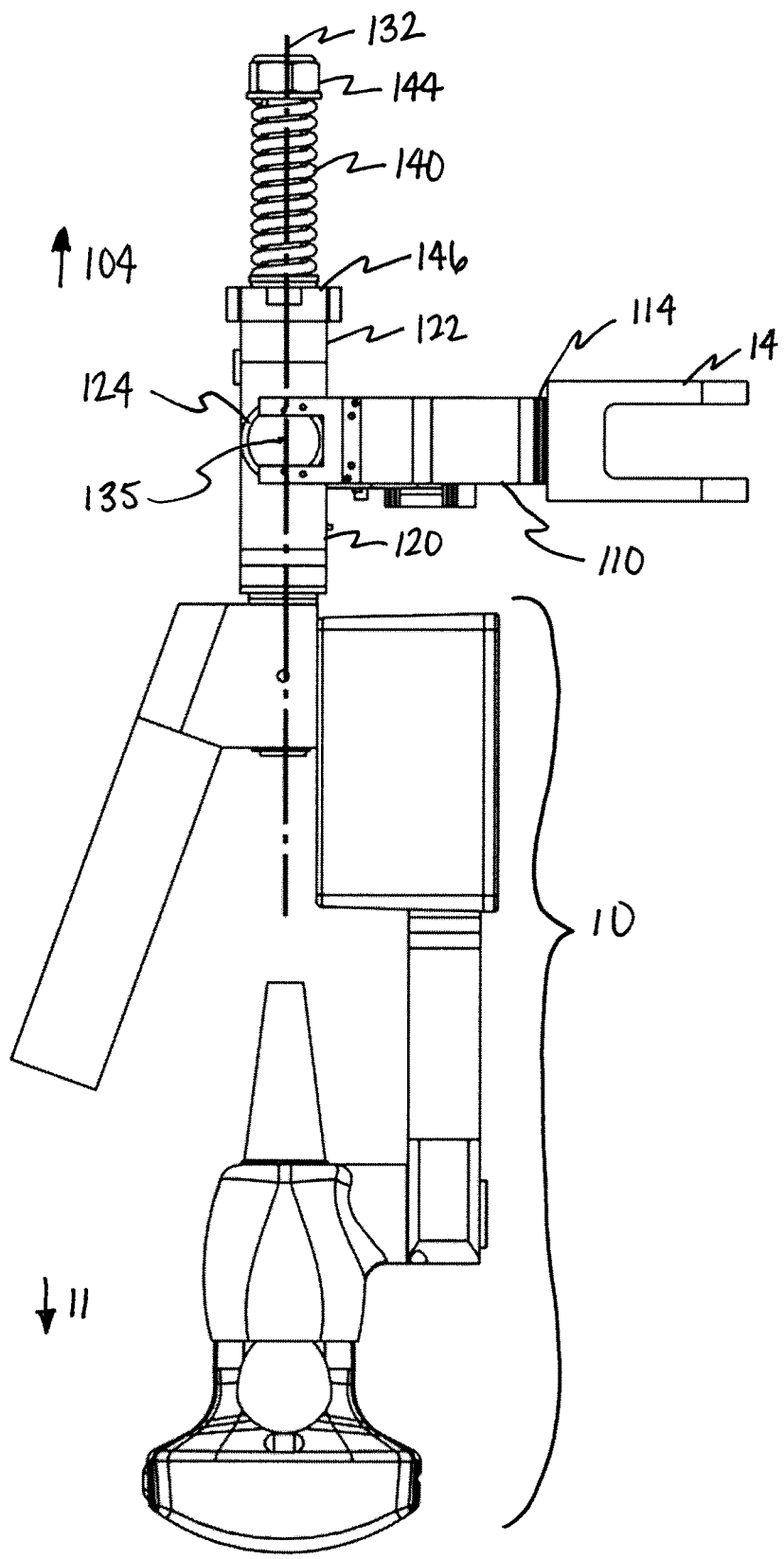
Figure 6C:
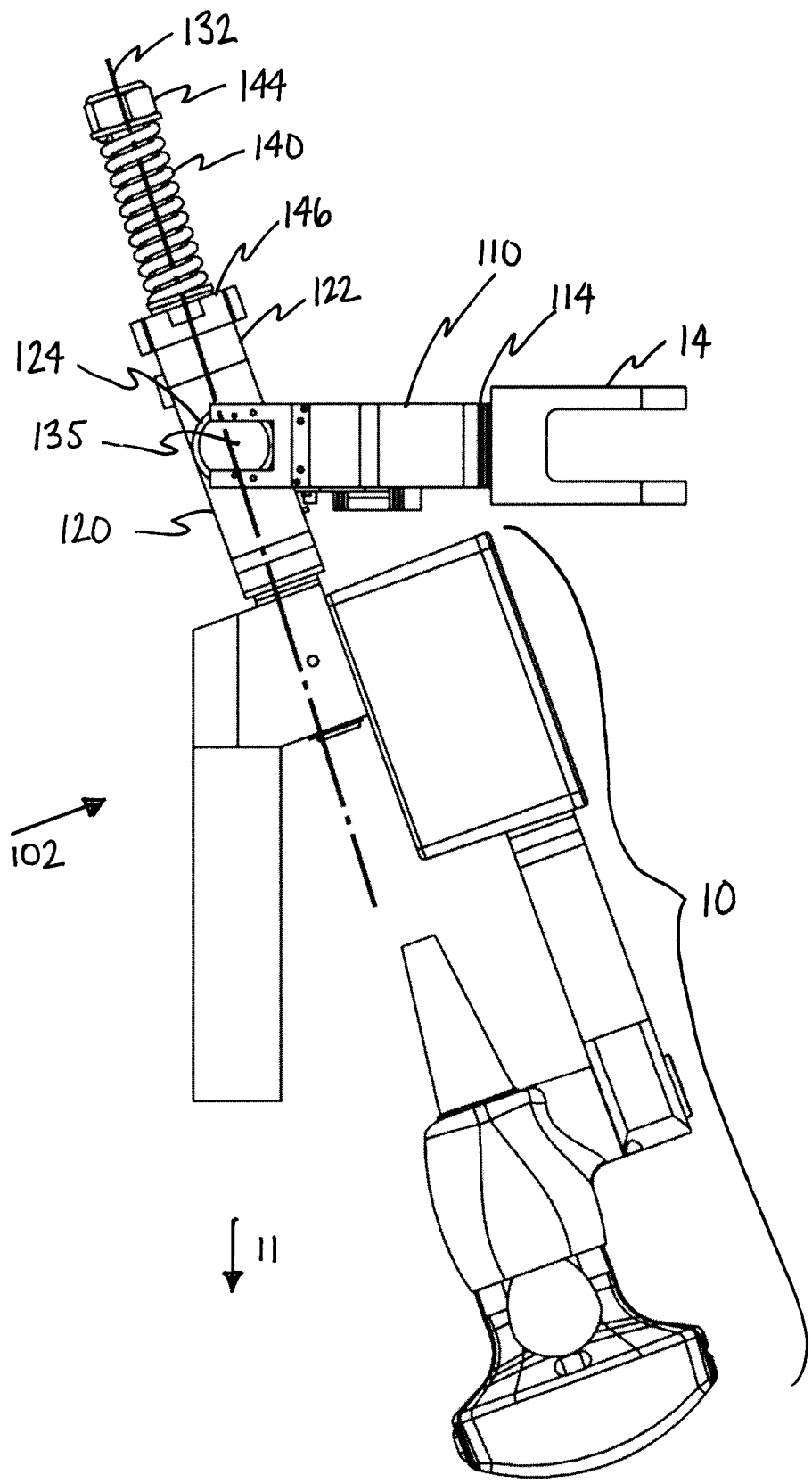

Referring to FIG. 6ABC, there is depicted the apparatus 100 pivoting about the pitch axis (i.e., second axis) from left to right across the page. As shown in FIGS. 6A and 6C, rotation of the apparatus 100 to the left or right of the page about the pitch axis 131 (not shown) will cause the counterbalance axis 132 to diverge from the counterbalance point 135 creating a moment or torque to produce the counterbalancing torque 102 in a direction of the z-axis and having a given magnitude to counterbalance the torque produced by the load vector 11 associated with the payload 10. FIG. 6B depicts the apparatus 100 in position such that the counterbalance axis 132 is aligned with the counterbalance point 135. While no torque is produced by the resilient member 140 or the payload 10, the member 140 produces a net force 104 having a given magnitude to support the load vector 11 associated with the payload 10.

Each of the roll axis 130 and pitch axis 131 may also preferably, but need not necessarily, be adapted for individual braking or tracking with rotary encoders (not shown). Rotatory encoders may be understood by persons skilled in the art to be devices used to measure the rotation of shafts that may be rigidly attached to arms 110, 120. By mounting encoders onto the arms 110, 120 of the apparatus 100, it may be possible to determine the pose of the arms 110, 120 and calculate the position of the payload 10 in space. In some embodiments, the range of motion of the roll axis 130 may preferably, but need not necessarily, be about less than or equal to 180 degrees inwards and about less than or equal to 180 degrees outwards, while the range of motion of the pitch axis 131 may preferably, but need not necessarily, be about plus/minus 180 degrees. The range of motion in the pitch axis 131 may depend on the payload 10 to be supported and may further be limited by, for example, any cables that may be attached thereto.

Figure 7:
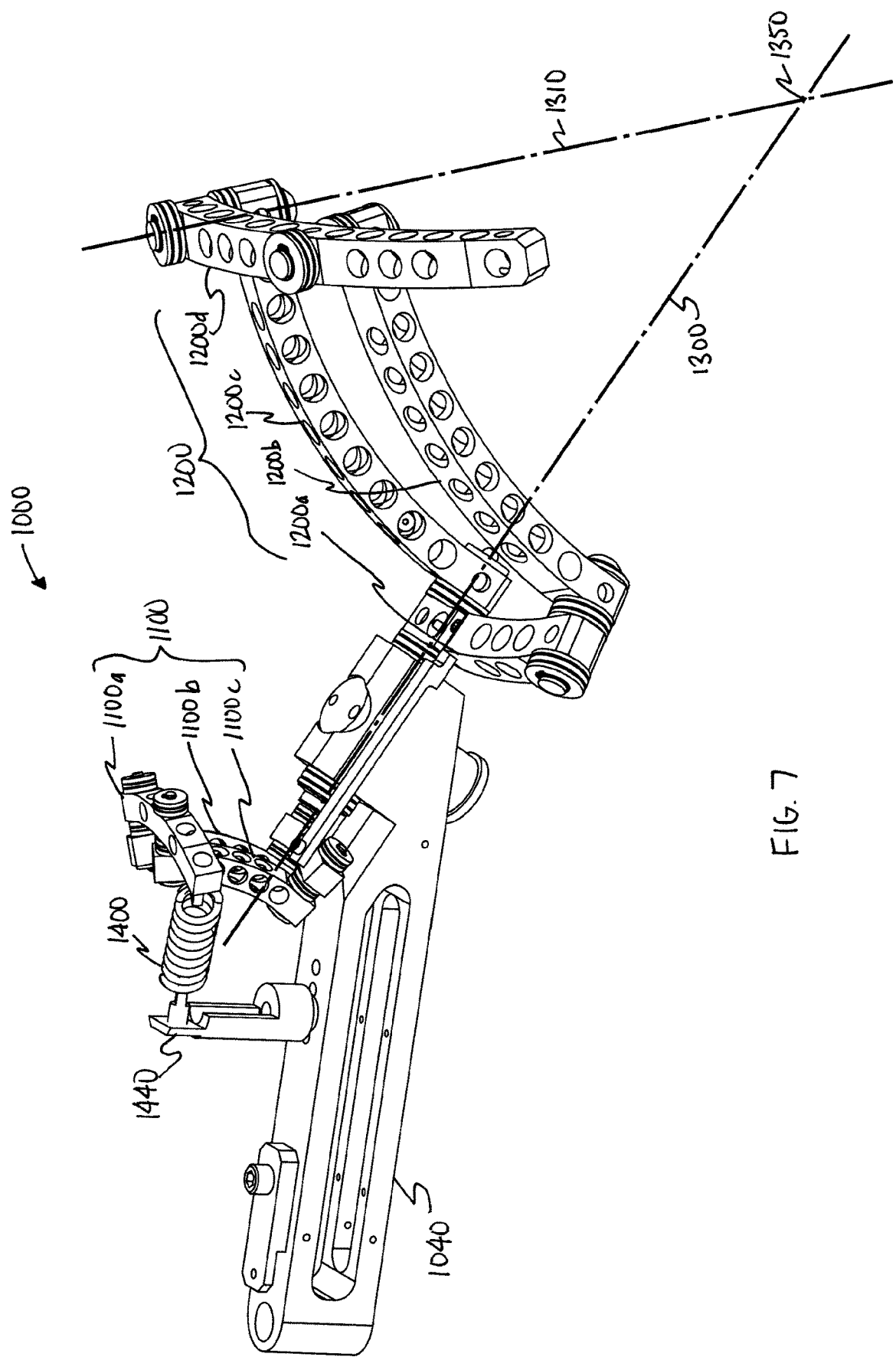
FIG. 7 is a perspective view of an alternate embodiment of the invention with an RCM.

FIG. 7 presents an alternative embodiment of the invention 1000 using a spherical linkage comprising a plurality of spherical links forming a first spherical link 1100 and a second spherical link 1200. The first spherical link 1100 comprises links 1100*a,b,c* that are preferably pinned together to allow for rotation about a first axis 1300. In this alternative embodiment, the payload (not shown) preferably engages the second spherical link 1200. The second spherical link 1200 comprises links 1200*a,b,c,d* that are preferably pinned together to allow for rotation about a first axis 1300. In the present embodiment, link 1200*a* is also a component of the first spherical link 1100. Link 1200*a* preferably rigidly attaches to the first spherical link 1100, for example, using a crossbar positioned parallel to the first axis 1300. The second spherical link projects a second axis 1310 (as seen in FIG. 7) that intersects with the first axis 1300 at a counterbalance point 1350 (i.e., an RCM). Spherical link 1200*c* is preferably rigidly attached to link 1100*b*. Spherical link 1100*b* may preferably, but need not necessarily, be attached to link 1200*c* such that the respective movement of link 1100*b* in relation to link 1200*c* is a mirror image. A resilient member 1400, preferably but need not necessarily an extension spring, is attached between a preload member 1440 on a mounting bracket (or ground) 1040 and the first spherical arm 1100. The extension spring preferably, but need not necessarily, functions as a non-zero length spring counterbalance. The "k" value of the spring and the geometry of the counterbalance are preferably defined by equation (1). The second spherical arm 1200 and payload (not shown) are preferably counterbalanced by the spring acting on the first spherical arm 1100. Accordingly, in this alternative embodiment, the payload (not shown) may be attached to the apparatus 1000 at a position distal to the RCM and still be counterbalanced as its orientation is manipulated.

The present invention may have a wide range of applications in both the medical and industrial fields. In preferred embodiments, the apparatus can be used to assist human operators in situations where difficulties are encountered positioning tools or payloads. The apparatus of the present invention preferably provides a fully counterbalanced method of positioning a tool or payload at a desired orientation. The apparatus may greatly reduce the effort exerted by an operator to perform tasks involving a given payload. This reduced effort may be beneficial for operators who are required to orientate heavy payloads or perform repetitive motions. The apparatus preferably, but need not necessarily, maintains an orientation if the payload is released by an operator. If a tool must be maintained at a fixed position for prolonged periods, the operator is preferably not required to exert any effort to maintain the pose. The apparatus may preferably also be fully encoded to track the orientation of the arms. Tracking data for the apparatus is useful for applications requiring payloads to be positioned at specific orientations.

In some embodiments, the apparatus may be mounted onto a previously developed backbone arm. The apparatus mounted onto the backbone preferably, but need not necessarily, provides a fully counterbalanced mechanical mimic of a human arm. The previous backbone may preferably mimic the shoulder, upper arm, elbow and forearm and may allow for gross translation of a payload. The apparatus may preferably, but need not necessarily, mimic the human wrist and may allow for the orientation and angulation of the payload. The combined backbone and wrist may preferably be used for tasks where a human operator's arm is normally used. Since the mechanical arm is fully counterbalanced, it preferably greatly reduce the strain experienced by operators arising from awkward motions, heavy payloads or repetitive actions. The mechanical arm may preferably contribute to improved worker ergonomics and reduce workplace injuries.

The present invention may also be applied in the design of automated robotic systems. The two rotational axes of the apparatus may preferably, but need not necessarily, be motorized. Small, lightweight, and low torque motors may preferably be used to motorize the apparatus since the resilient member (e.g., spring) counterbalance may greatly reduce the force required to actuate the rotational axes. Furthermore, in the event of a power failure the apparatus will preferably maintain the motorized apparatus' position so that it will not slump as may be common in traditional robotic systems. The apparatus in combination with the backbone mechanical arm may also be motorized and used as an automated robotic system. The combined arm would offer the same safety benefits of lightweight motors and safety as the standalone apparatus.

The embodiments presented herein were preferably, but need not necessarily, developed for use in 3D ultrasound guided liver ablations. The apparatus is preferably intended to be mounted onto the end of a known backbone arm. The payload of the apparatus may, in preferable embodiments, be a mover which moves a 2D ultrasound transducer in order to acquire 3D ultrasound images. A needle guidance system may optionally be incorporated into the payload. 3D ultrasound images may preferably, but need not necessarily, be used to guide needles to targets within the liver to perform ablations. The prior art arm preferably supports the weight of the payload (e.g., the transducer and mover) reducing the effort by the user (e.g., physician) to acquire images. The prior art arm may also allow the user (e.g., physician) to move the transducer away from the patient and return to the same position as part of the procedure workflow.

The spring counterbalance may be based on U.S. Patent Application No. 2010/0319163, herein incorporated by reference, which may have been applied in the resilient member counterbalance for the prior art backbone arm and may have been used in the design of the apparatus of the present invention. U.S. Patent Application No. 2010/0319163 may have used two resilient members to achieve counterbalance for a payload moving over a range of motion of ±90 degrees to the horizontal. However, the 3D ultrasound guided liver ablation application may require the probe to be able to move beyond 90 degrees to horizontal, which the counterbalance disclosed in U.S. Patent Application No. 2010/0319163 may have been adapted to support. The counterbalance of the prior art may either require a third spring or a specialized mechanism that allows one of the springs to act in both compression and extension. This modified prior art counterbalance would have required a bulky and heavy solution to successfully integrate into the wrist. The previous counterbalance design was not ideal for the ultrasound guided liver ablation application.

The apparatus presented in the present disclosure provides a very compact solution for a counterbalanced wrist. The requirements for the liver ablation system specify a small and compact wrist design. Notably, only a single resilient member is required in the present design disclosed. The design requirements for size could not have been achieved using the previously disclosed multiple spring balance design. Furthermore, the quality of the counterbalance in the wrist is preferably not compromised with the compact design of the present invention. Both the previous multiple spring counterbalance and the zero-free length spring counterbalance design yield theoretically exact solutions. The primary drawback of the present invention, however, may be adjustability. The multiple spring counterbalance may be adjusted to support a wide range of payloads by turning a single nut. In contrast, the single resilient member design of the present invention may only support payloads having a fixed mass. Fine tuning of the apparatus of the present invention may be achieved through the payload adjust blocks described. However, for large changes in the load vector associated with the payload, the resilient member must be swapped in the apparatus.

The foregoing description has been presented for the purpose of illustration and is not intended to be exhaustive or to limit the invention to the precise form disclosed. Other modifications, variations and alterations are possible in light of the above teaching and will be apparent to those skilled in the art, and may be used in the design and manufacture of other embodiments according to the present invention without departing form the spirit and scope of the invention. It is intended the scope of the invention be limited not by this description but only by the claims forming a part hereof.

The embodiments for which an exclusive privilege or property is claimed are as follows:

1. A counterbalance apparatus, providing a center of motion having at least two axes of rotation for a payload supported distal to the center of motion in which the payload has a load vector applied in a direction of the vector of gravity, the apparatus comprising:
   a gimbal configured to support the payload and allow the payload to have rotational movement about the center of motion, wherein a load torque is applied to the gimbal by the rotational movement of the payload about the center of motion along one or more of the axes of rotation;
   a resilient member configured to engage the gimbal to thereby supply a support torque about the center of motion along the one or more of the axes of rotation to counterbalance the load torque applied to the gimbal by the rotational movement of the payload;
   a counterbalance post that defines a counterbalance axis, the counterbalance post engaged with the gimbal,
   wherein the resilient member is adapted to engage the gimbal and the counterbalance post such that the resilient member compresses or extends to create a torque in a direction of the counterbalance axis; and wherein the payload is a medical transducer.

2. The counterbalance apparatus of claim 1 with two or three gimbals.

3. The counterbalance apparatus of claim 2, in which the gimbals are mounted orthogonally.

4. The counterbalance apparatus of claim 1, in which the center of motion is internal or external to the apparatus.

5. The counterbalance apparatus of claim 1, in which the resilient member is adapted to produce an extension force or a compression force.

6. The counterbalance apparatus of claim 5, in which the resilient member is a spring.

7. The counterbalance apparatus of claim 6 in which the spring is a zero-length spring.

8. The counterbalance apparatus of claim 1, further comprising a preload member to engage the resilient member to alter a magnitude of the support torque, or counterbalance adjust blocks to alter the magnitude of the support torque.

9. The counterbalance apparatus of claim 1, in which rotation about a roll axis is about less than or equal to 180 degrees inwards and about less than or equal to 180 degrees outwards, and in which rotation about a pitch axis is about plus or minus 180 degrees.

10. The counterbalance apparatus of claim 1, further comprising a ball joint to facilitate engagement of the gimbal by the resilient member.

11. The counterbalance apparatus of claim 1, wherein the counterbalance post slides in the gimbal.

12. The counterbalance apparatus of claim 1, wherein the medical transducer is an ultrasonic transducer.

13. A method for supporting a payload using a counterbalance apparatus providing a center of motion having at least two axes of rotation for the payload supported distal to the center of motion in which the payload has a load vector applied in a direction of the vector of gravity, the method comprising:
   attaching the payload to a gimbal configured to allow the payload to have rotational movement about the center of motion, wherein a load torque is applied to the gimbal by the rotational movement of the payload about the center of motion along one or more of the axes of rotation;
   configuring a resilient member to engage the gimbal to thereby supply a support torque about the center of motion along one or more of the axes of rotation to counterbalance the load torque applied to the gimbal by the rotational movement of the payload;
   configuring a counterbalance post to engage with the gimbal, the counterbalance post defining a counterbalance axis;
   configuring the resilient member to engage both the gimbal and the counterbalance post such that the resilient member compresses or extends to supply the support torque in a direction of the counterbalance axis to counterbalance the load torque, and wherein the payload is a medical transducer.

14. The method of claim 13, in which the apparatus comprises two or three gimbals.

15. The method of claim 14, in which the gimbals are mounted orthogonally.

16. The method of claim 13, in which the center of motion is internal or external to the apparatus.

17. The method of claim 13, in which the resilient member is used to produce an extension force or a compression force.

18. The method of claim 17, in which the resilient member is a spring.

19. The method of claim 18 in which the spring is a zero-length spring.

20. The method of claim 13, further comprising use of a preload member to engage the resilient member to alter a magnitude of the support torque, or use of counterbalance adjust blocks to alter the magnitude of the support torque.

21. The method of claim 13, in which rotation about a roll axis is about less than or equal to 180 degrees inwards and about less than or equal to 180 degrees outwards, and in which rotation about a pitch axis is about plus or minus 180 degrees.

22. The method of claim 13, wherein the counterbalance post slides in the gimbal.

23. The method of claim 13, wherein the medical transducer is an ultrasonic transducer.

* * * * *